(12) United States Patent
Kraus (10) Patent No.: US 7,892,204 B2
(45) Date of Patent: Feb. 22, 2011

(54) MEMBRANE SUPPORT FOR DRIP CHAMBER

(76) Inventor: Menahem Kraus, 25 Pashosh Street, Rehovot 76100 (IL)

( * ) Notice: Subject to any disclaimer, the term of this patent is extended or adjusted under 35 U.S.C. 154(b) by 414 days.

(21) Appl. No.: 11/677,054

(22) Filed: Feb. 21, 2007

(65) Prior Publication Data

US 2007/0142790 A1   Jun. 21, 2007

Related U.S. Application Data

(63) Continuation-in-part of application No. 10/152,004, filed on May 22, 2002, now abandoned.

(51) Int. Cl.
*A61M 1/00* (2006.01)
(52) U.S. Cl. ................... 604/126; 604/122; 604/252
(58) Field of Classification Search ............ 604/82, 604/252, 122, 126, 251
See application file for complete search history.

(56) References Cited

U.S. PATENT DOCUMENTS

| 4,009,714 | A | * | 3/1977 | Hammer | 604/126 |
| 4,013,072 | A | * | 3/1977 | Jess | 604/252 |
| 4,116,646 | A | * | 9/1978 | Edwards | 96/6 |
| 5,779,674 | A | * | 7/1998 | Ford | 604/126 |

* cited by examiner

*Primary Examiner*—Nicholas D Lucchesi
*Assistant Examiner*—Brooke M Matney
(74) *Attorney, Agent, or Firm*—Dekel Patent Ltd.; David Klein (57) ABSTRACT

A drip chamber for intravenous infusion including a support member having a longitudinal axis, two ends and at least one support face distanced from both ends, a membrane joined to the at least one support face, and a support member outlet formed in the support member and in fluid communication with the membrane, the support member outlet including a bore and being fluidly communicable with an outlet of the drip chamber.

12 Claims, 7 Drawing Sheets

MEMBRANE SUPPORT FOR DRIP CHAMBER

CROSS RELATION TO OTHER APPLICATIONS

This application is a continuation-in-part of U.S. patent application Ser. No. 10/152,004, filed May 22, 2002, now abandoned and claims priority therefrom.

FIELD OF THE INVENTION

The present invention relates generally to drip chambers used with intravenous infusion sets and particularly to membrane supports for such drip chambers.

BACKGROUND OF THE INVENTION

Intravenous infusion sets commonly include drip chambers (DCs) to enable the flow rate of an infusion liquid to be visually observed. In a typical installation, an infusion bag is suspended above a patient and a spike at an inlet of the DC pierces the bag, whereby the infusion liquid drips into the DC. The flow rate of the infusion liquid may be observed by the rate of formation of drops of the liquid from the inlet into the DC down through an outlet of the DC which is connected to tubing to the patient. The DC helps prevent air from entering the downstream tubing. This is achieved by a liquid layer acting as an air barrier at the bottom of the chamber. It is formed by manual "priming" (squeezing) of the chamber before the start of infusion.

Commercial drip chambers are constructed simply of a flexible, transparent cylinder with inlet and outlet. They also often contain a screen at the bottom, acting as a coarse filter preventing particles from entering the vein.

It is desirable to have a finer filter such as a hydrophilic membrane, ideally a bacteria retentive membrane, incorporated into the DC. This is advantageous in that it obviates the use of an extra filter often connected downstream of the infusion set. More importantly, such a membrane has the advantage of solving the following problem often encountered in infusion. When the infusion bag empties, so does the DC. As the above mentioned liquid layer is now absent, air enters the tubing downstream of the DC. This necessitates opening the system and re-priming the set before infusion can be continued. By using a hydrophilic membrane at the DC outlet, liquid flow is not impeded, yet air intrusion is substantially prevented at all pressures below the membrane "bubble point". Thus after the infusion bag empties a new bag can be connected and infusion restarted without need for re-priming.

A few patents (e.g., U.S. Pat. Nos. 4,013,072, 4,521,212 and 5,902,281, the disclosures of which are incorporated herein by reference) have described infusion devices that include membranes; however no simple, membrane-based infusion set is available commercially. The reasons for this are both technological and commercial. Membranes are sensitive structures and may easily be affected by solvents, glues and other bonding means. Also infusion sets need to conform to certain flow and accuracy criteria which may be affected by the membrane. Additionally the infusion set must remain inexpensive even with the membrane incorporated.

Another infusion device with a membrane is described in U.S. Pat. No. 5,779,674 to Ford. In this device, a hydrophilic membrane is attached to a support structure and may be horizontally or vertically oriented. However, this device has a drawback of the membrane being situated close to a base which is bonded with an adhesive to a drip chamber, meaning that the membrane can possible come into contact with the adhesive. In addition, the structure of the membrane support is such that air entrapped downstream of the membrane between the membrane and drip chamber outlet, can occasionally escape into the infusion line, thus defeating the whole purpose of the membrane drip chamber.

The need therefore exists for an economical, accurate, high throughput, membrane-containing drip chamber that poses no danger of air escaping into the infusion line.

SUMMARY OF THE INVENTION

The present invention seeks to provide an improved membrane support that permits safe mounting of a membrane, e.g., a hydrophilic or bacterially retentive membrane, into a drip chamber with no danger of contaminating or ruining the membrane with adhesive and the like. The membrane support includes a support member that supports the membrane at a safe distance from ends of the support member which are bonded to the drip chamber with adhesive, or by friction. The seal between the membrane support and the drip chamber prevents direct fluid communication between the volume upstream of the membrane and the drip chamber outlet. Only liquid permeating through the membrane may reach the outlet. In one embodiment, the membrane is generally perpendicular to a longitudinal axis of the drip chamber. In another embodiment, the membrane is generally parallel to the longitudinal axis. The latter embodiment permits using a membrane with a significantly larger surface area and is particularly useful for a bacterially retentive membrane. The drip chamber may be constructed such that liquid may be in contact with the membrane even when the drip chamber may be oriented upside down.

There is thus provided in accordance with an embodiment of the present invention a drip chamber for intravenous infusion including a support member having a longitudinal axis, two ends and at least one support face distanced from both ends, a membrane joined to the at least one support face, and a support member outlet formed in the support member and in fluid communication with the membrane, the support member outlet including a bore and being fluidly communicable with an outlet of the drip chamber.

The drip chamber may further include a filtrate outlet located at an upper portion of the support member, the support member being formed with a conduit which fluidly connects the filtrate outlet to the support member outlet. The support member may be bonded to the drip chamber with an adhesive, the adhesive not contacting the membrane. The membrane may be hydrophilic. The membrane may be bacterially retentive. The membrane may have a surface area of at least about 5 $cm^2$. The support member outlet may be connectable to downstream tubing of an infusion set. The at least one support face may be generally parallel or perpendicular to the longitudinal axis.

There is also provided in accordance with an embodiment of the present invention a supported membrane assembly for joining into a drip chamber including a support member having a longitudinal axis, two ends and at least one support face distanced from both ends, a membrane joined to the at least one the support face, and a filtrate outlet located at an upper portion of the support member.

The supported membrane assembly may further include a support member outlet formed in the support member and in fluid communication with the membrane, the support member outlet being fluidly communicable with an outlet of a drip chamber, and wherein the support member may be formed with a conduit which fluidly connects the filtrate outlet to the support member outlet. The support member outlet may be connectable to downstream tubing of an infusion set.

There is also provided in accordance with an embodiment of the present invention a drip chamber for an intravenous infusion set including a drip chamber body and an outlet, and a supported membrane assembly connectable to the drip chamber, the supported membrane assembly including at least one membrane and a support member, the support member including a liquid outlet joined inside the drip chamber outlet. A filtrate outlet may be located at an upper portion of the support member.

In accordance with an embodiment of the present invention the drip chamber may include a housing made of a non-PVC material.

There is also provided in accordance with an embodiment of the present invention an intravenous infusion set including an infusion bag, a non-vented drip chamber, tubing and clamp on the tubing, the drip chamber including a supported membrane assembly, wherein the drip chamber and the infusion set are automatically primed when the clamp may be opened.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
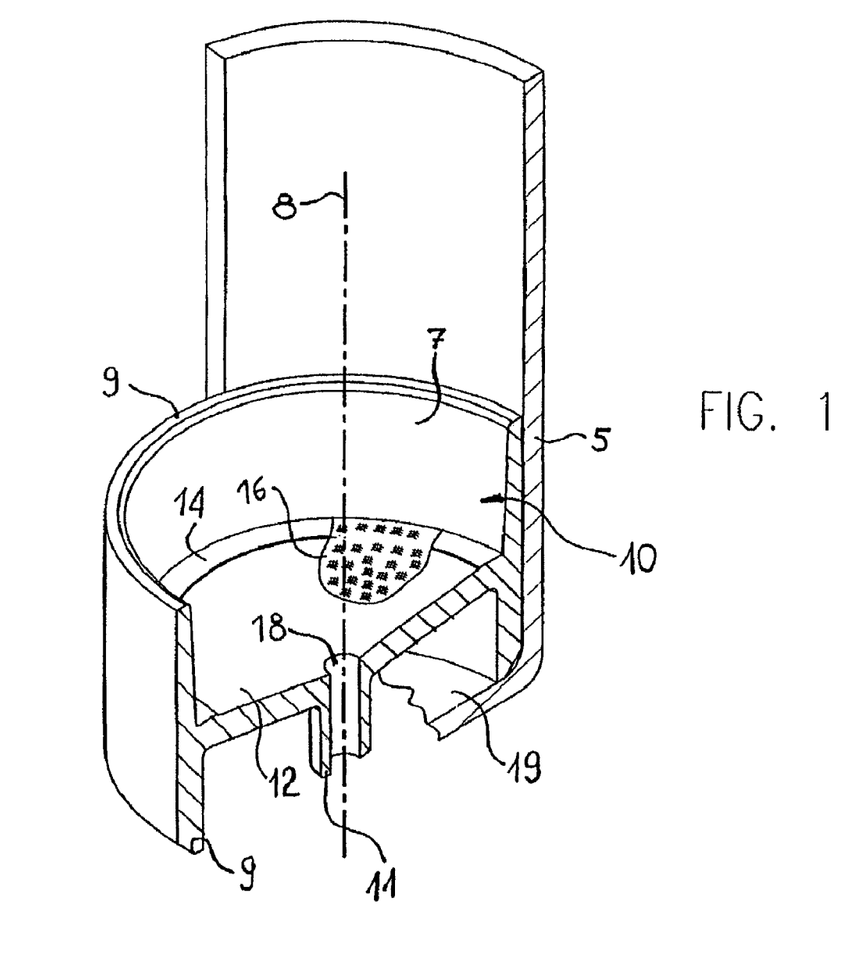
FIG. 1 is a simplified pictorial illustration of a membrane support and drip chamber, constructed and operative in accordance with a preferred embodiment of the present invention.

Reference is now made to FIG. 1 which illustrates a drip chamber 5 and membrane support 10, constructed and operative in accordance with a preferred embodiment of the present invention.

Membrane support 10 includes a support member 7 preferably constructed of a short, open-ended cylinder with a central, generally circular support surface 12, most preferably integrally formed therewith, such as by injection molding. Support member 7 has a longitudinal axis 8 and two ends 9.

Support surface 12 extends inwards from an inner wall of the support member 7 at a distance from both ends 9. Support surface 12 may be slightly conical in shape, although it is appreciated that any arbitrary shape may be used. Support surface 12 preferably has a peripheral rim 14 to which a generally circular membrane 16 (shown partially in FIG. 1) can be joined. As used herein, reference to two materials or elements being "joined" refers to the situation wherein the two materials or elements are directly joined to one another or where they are indirectly joined to one another such as where both are joined to an intermediate element. Similarly, methods of joining two materials or elements include forming the elements or materials integrally, or attaching the elements together such as through the use of sonic or thermal bonding, welding, and the like.

An outlet 11 preferably extends from support surface 12 and is formed with a bore 18. Outlet 11 is connectable to downstream tubing (not shown) of an infusion set (not shown). Membrane support 10 is preferably bonded to DC 5 by applying a small amount of adhesive to a bottom surface 19 of DC 5. The adhesive is never in close contact with membrane 16 and possible damage is minimized.

DC 5 is connected to an infusion bag (not shown) in the usual manner. When DC 5 is first primed, membrane 16 wets within a few seconds. Thereafter air cannot escape DC 5 at pressures below the bubble point of membrane 16. This bubble point pressure varies according to membrane pore size and can be chosen over a wide range, for example 0.05-5 atm. For a typical infusion set use, a bubble point pressure of 0.5-1 atm will be suitable, corresponding to a pore size rating of 1-5 µm.

Upon emptying of the infusion bag, liquid level in DC 5 will recede and reach exactly the height of membrane 16. No air will penetrate below membrane 16. Thus the downstream infusion line will remain primed. A new bag can, therefore, be connected upstream of DC 5 and infusion continued with no need for repriming.

In another embodiment of the invention, membrane 16 may be a bacterially retentive membrane. Such membranes have a pore size rating of 0.2 µm and below and are capable of retaining most known bacteria even at high volume concentration. Such a membrane can be built into DC 5 with its generally circular configuration, as described above. However, this configuration is generally not suitable for bacterially retentive membranes, because such membranes are quite "tight" and therefore provide relatively low liquid throughputs. The surface area provided by the circular configuration (about 1 cm.sup.2) is too small for either gravity or pump driven infusion.

Figure 2:
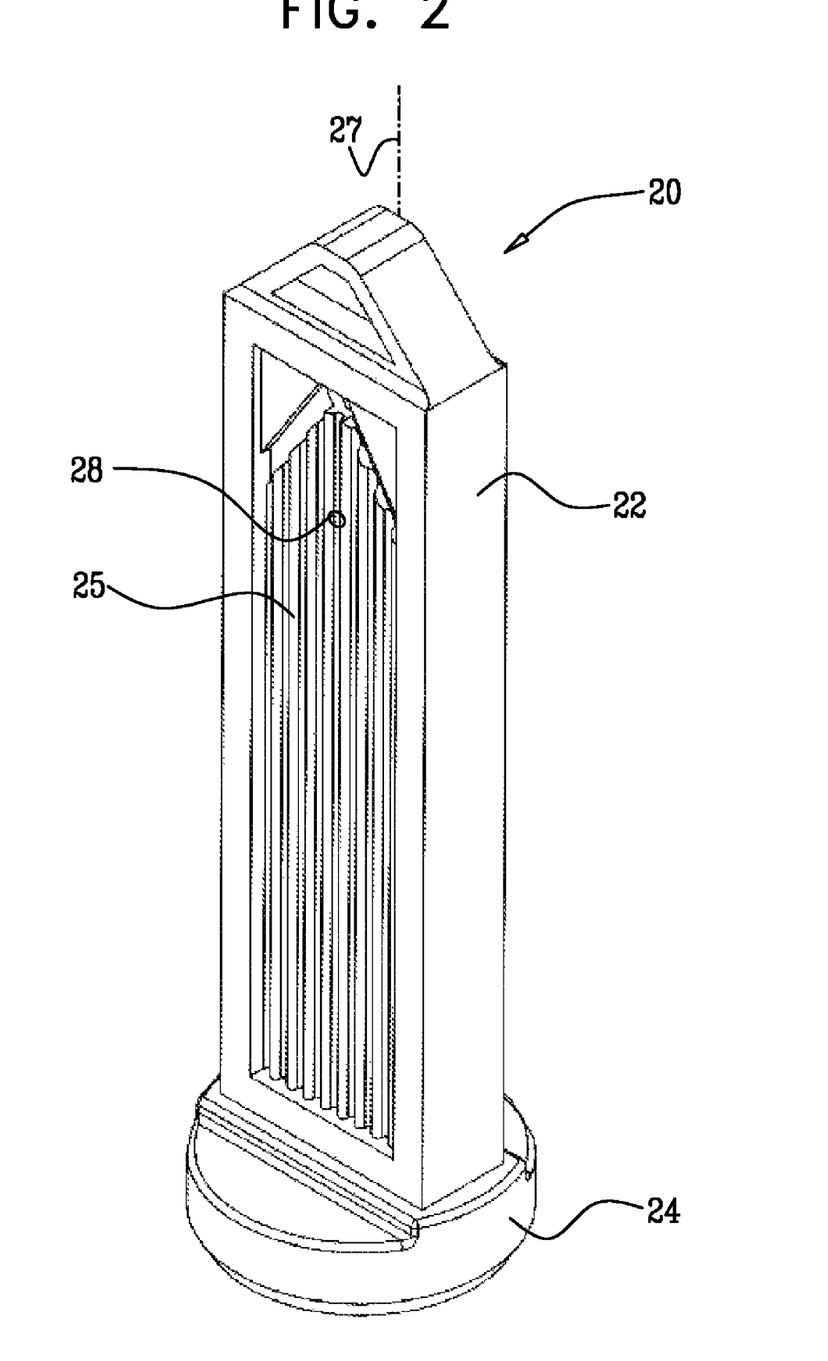
FIGS. 2 and 3 are simplified pictorial and cutaway illustrations, respectively, of a supported membrane assembly, constructed and operative in accordance with another preferred embodiment of the present invention.
Figure 3:
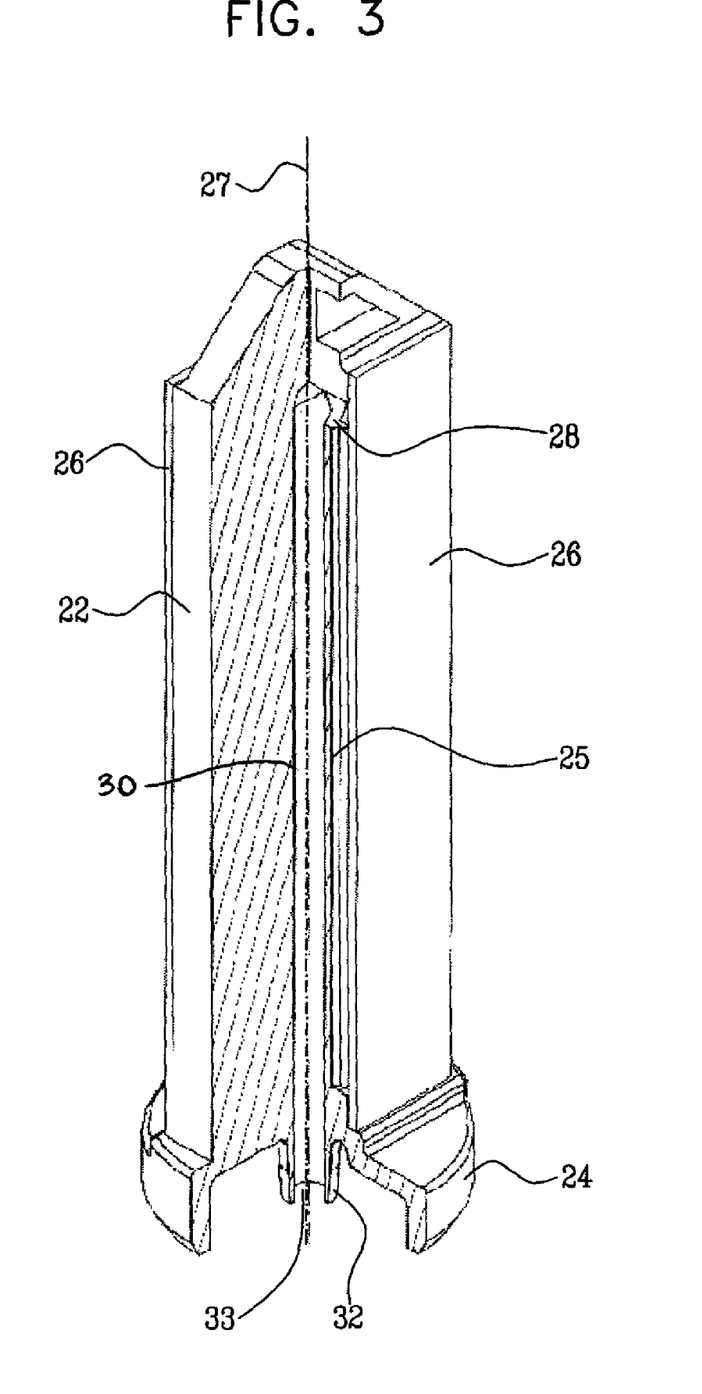

Reference is now made to FIGS. 2 and 3 which illustrate a membrane support 20 constructed and operative in accordance with another preferred embodiment of the present invention. In membrane support 20, the membrane area is substantially increased by arranging the membrane surface generally parallel to the DC longitudinal axis, instead of perpendicular as in the embodiment of FIG. 1, as is now described. The increased membrane area is a significant advantage because it enables use of bacterially retentive membranes with good liquid throughputs.

Figure 4:
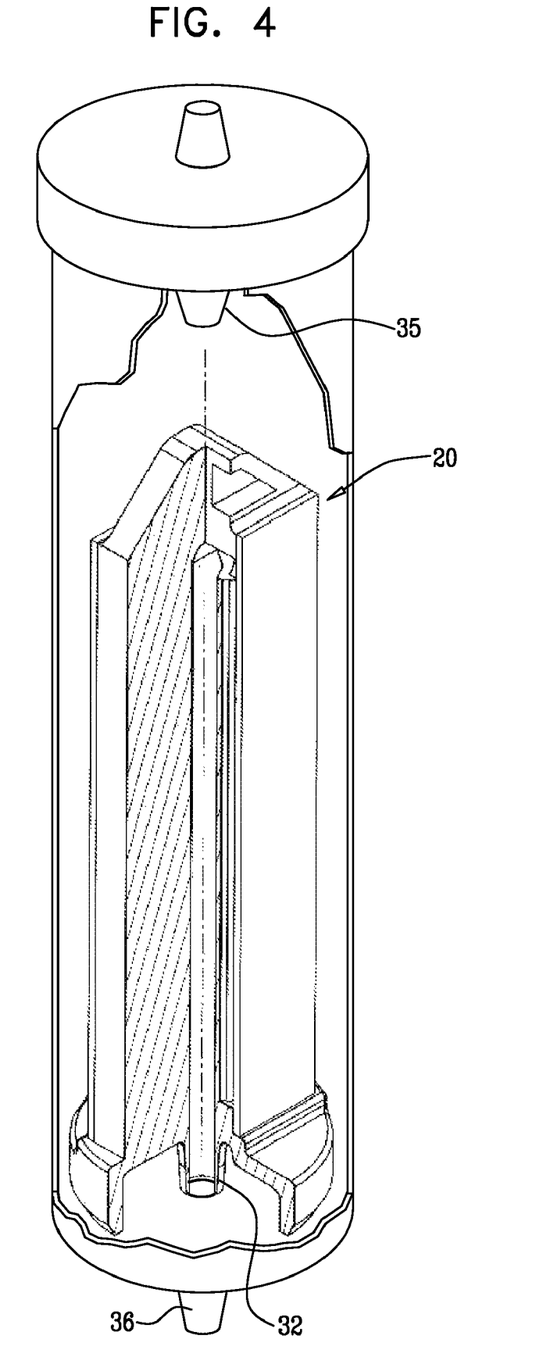
FIG. 4 is a simplified pictorial illustration of the supported membrane assembly of this invention joined inside a drip chamber.

Supported membrane assembly 20 preferably includes an upright, generally rectangular support member 22 with a generally circular base 24. A membrane 26 is joined to one or both large support faces 25 (FIGS. 2 and 3) of support member 22. A membrane surface area of 5-10 cm$^2$ can easily be achieved in this embodiment. The membrane surface is generally parallel to a longitudinal axis 27 of membrane support 20 and a drip chamber 34 (shown in FIG. 4 with drop former 35 and an outlet 36, both well known in the art of drip chambers). A filtrate outlet 28 (FIGS. 2 and 3) is preferably located at an upper portion of support member 22 in order to drain all air from the volume downstream of membrane 26. Filtrate can flow from filtrate outlet 28 via a conduit 30 to an outlet 32. Outlet 32 is preferably formed with a bore 33 and is in fluid communication with outlet 36 of a preformed drip chamber (FIG. 4), or is directly connectable to downstream tubing (not shown) of an infusion set (not shown) when the drip chamber is a bottomless cylinder joined to circular base 24 of the membrane support.

Figure 5:
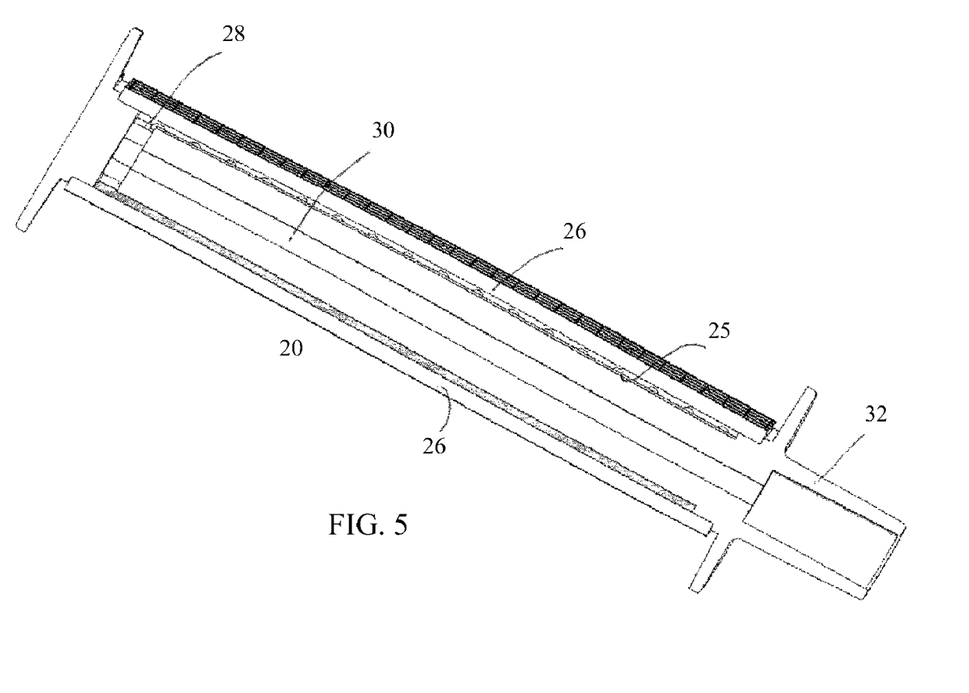
FIG. 5 is a simplified cross section of a supported membrane assembly, showing the downstream liquid passages.

FIG. 5 is a cross section of supported membrane assembly 20 showing support face 25, membrane 26, filtrate outlet 28, filtrate conduit 30 and outlet 32. Upon priming of the supported membrane assembly-containing drip chamber, as liquid enters the space between the membrane support 25 and membranes 26, all air in that space will rise and escape through outlet 28, conduit 30 and outlet 32. Since this downstream volume consists of relatively narrow passages, flow will follow a "plug flow" regime, ensuring that all air in this downstream volume will be removed in an orderly manner.

As similarly described above for the embodiment of FIG. 1, supported membrane assembly 20 is preferably bonded to a DC 34 (FIG. 6) by applying a small amount of adhesive to a bottom surface of the DC. The adhesive is never in close contact with membrane 26 and possible damage is minimized.

Figure 6:
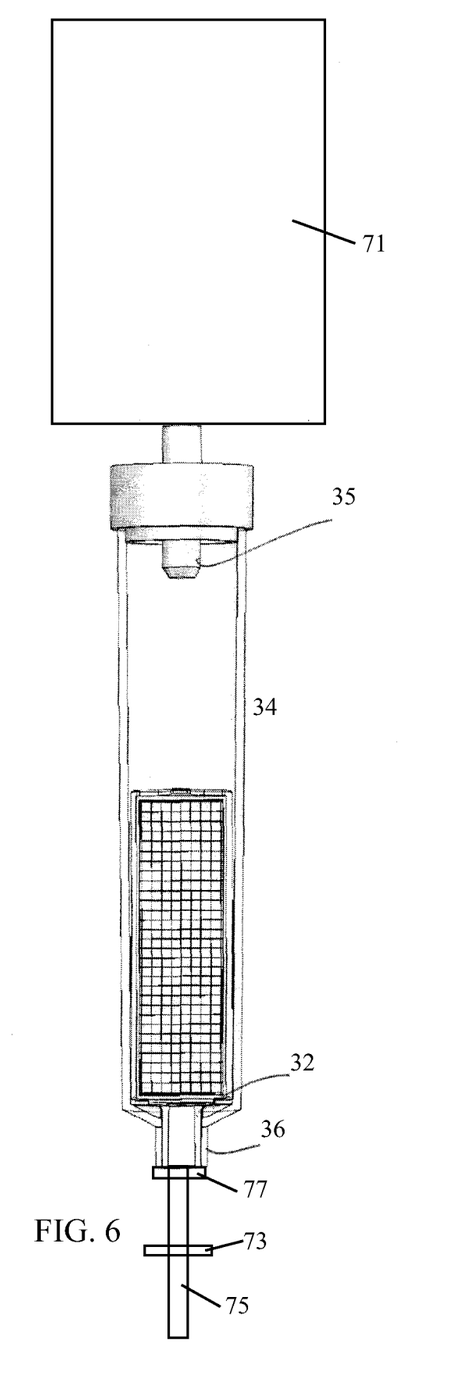
FIG. 6 is a pictorial illustration of a preferred mode of joining the supported membrane assembly to a drip chamber.

Alternatively supported membrane assembly 20 may be joined to the drip chamber, by making outlet 32 of dimensions such as to tightly fit into the drip chamber outlet 36 (FIG. 6). The advantage of this new joining mode is that it utilizes a small, relatively rigid area of the drip chamber, ensuring a good, permanent, air-tight, pressure resistant fit even without adhesive.

Figure 7:
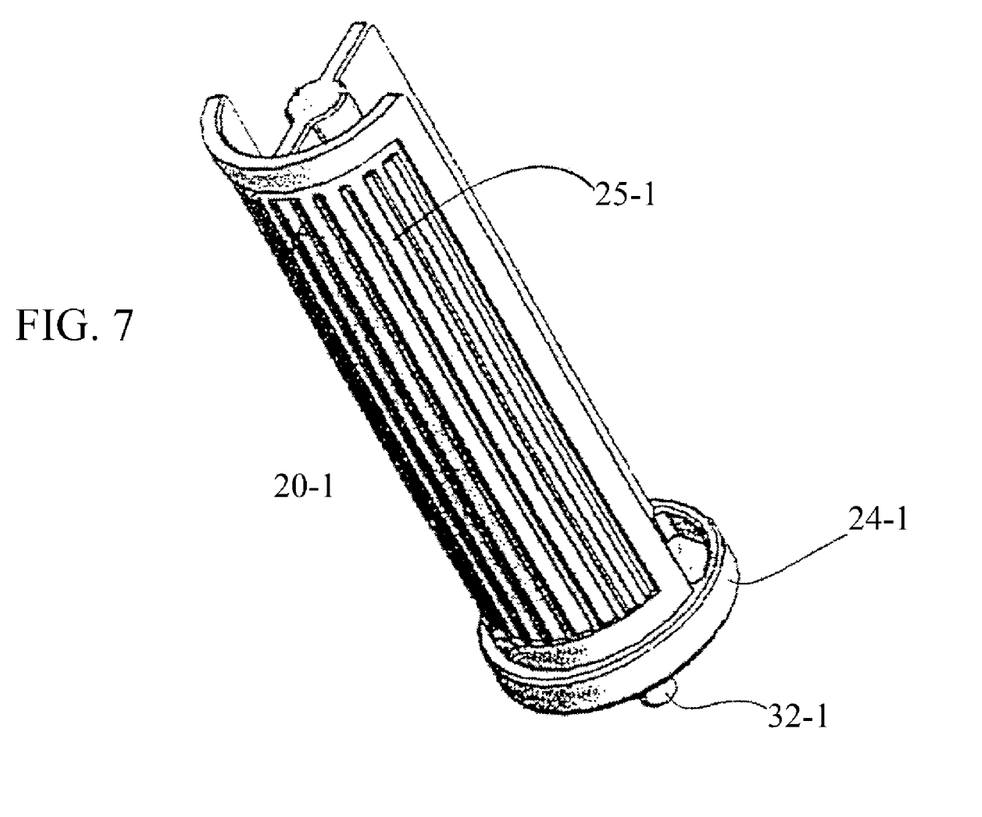
FIG. 7 is an illustration of a membrane support according to another preferred embodiment of the present invention.

In an alternate configuration the membrane support is in the shape of a half-cylinder (FIG. 7), having a support surface 25-1, circular base 24-1 and outlet 32-1. This configuration provides a higher membrane area than a flat rectangle.

Using the configuration of FIGS. 2 to 7, high gravity infusion flow rates are achievable. Using certain membranes in this configuration, flow rates conforming to international standards for infusion sets may be achieved. In pump driven infusion, little effect on pump accuracy is seen. Moreover, supported membrane assemblies of this invention help solve another problem associated with infusion by pump. All infusion pumps have alarms activated whenever air reaches the pump. Therefore, there is no risk that such air will reach the patient's vein. However, in order to continue infusion one needs to disconnect the set from the patient (with concomitant contamination risk), re-prime the set and reconnect. As the device of this invention prevents air from entering the set below the drip chamber, air will not reach the pump's air detector.

The configuration of FIGS. 2 and 3 has an additional advantage. Standard DC's are limited to an upright configuration. Turning the DC upside down will cause the trapped air to dangerously escape into the infusion line, and infusion fluid to fill the DC completely. The embodiment of FIG. 1 can prevent air loss. However that embodiment will not function in an upside-down orientation because air will contact the air-impermeable membrane 16.

In contrast, the embodiment of FIGS. 2 and 3 prevents air escape and may function in all orientations. When properly primed, liquid will be in contact with membrane 26 in both the upright and turned-over configurations. This DC is therefore suitable also for emergency use, where an upright orientation cannot always be assured.

Another advantage of the configuration of FIGS. 2-6 is automatic priming. Whereas in conventional infusion sets the drip chamber must be squeezed repeatedly during priming, an infusion set of this invention primes automatically. Certain drip chambers in the art prime automatically by utilizing a venting mechanism (e.g., U.S. Pat. No. 5,779,674). Drip chambers of this invention achieve this without vent.

As liquid is allowed to enter from an infusion bag 71 (FIG. 6) to the supported membrane assembly-containing drip chamber (by opening a clamp 73 on the tubing 75 below the drip chamber), air will escape from the drip chamber while liquid level rises. This will continue until the liquid reaches the height of filtrate outlet 28. The residual air in the upper part of the drip chamber is then trapped, thus completing priming of the drip chamber. The whole infusion set may be automatically primed simultaneously, if a removable membrane vent 77 is placed at the distal end of the tubing: infusion liquid flowing from the drip chamber will cause air to escape through the vent until the tubing is completely filled. Thus the whole set, including drip chamber and tubing is primed fully and automatically by simply opening one clamp.

It was surprisingly found that some common drip chamber materials of construction are not ideally suited for membrane-containing drip chambers. Thus soft PVC-based membrane drip chambers were found to occasionally lose functionality due to membrane wettability loss. This phenomenon was not seen in non-PVC chambers. While not being bound by any theory, this may be due to plasticizer migration from the drip chamber material onto the membrane.

For example, identical supported membrane assemblies were joined inside drip chambers with a drip chamber housing made of PVC, and styrene-butadiene drip chambers. All assembled drip chambers were placed in an oven at 70° C. In the PVC drip chamber the membrane lost wettability within 2-3 days. In the non-PVC drip chamber the membrane maintained its wettability indefinitely.

Two examples of tests performed with the above described embodiments are now described.

EXAMPLE 1

Gravitational Flow Rate

A membrane-containing drip chamber (MDC) was constructed in accordance with the embodiment of FIG. 1. An 8 μm rated nitrocellulose membrane was welded into the cylindrical insert. The MDC was incorporated in a standard infusion set. The gravitational flow rate was measured by connecting the set to an infusion bag containing saline and setting the outlet 1 m below the bag.

Flow rate ranged between 125 ml/min and 160 ml/min. The rate remained above 100 ml/min after 5 months of aging at 50° C. This rate conforms to International Standard for Infusion Equipment ISO 8536-4 (1998).

In order to test prevention of air intrusion, the set was opened to the atmosphere. No air leaked into the downstream line for at least 8 hours.

EXAMPLE 2

Bacterial Challenge

An MDC was constructed in accordance with the embodiment of FIGS. 2 and 3, using a 0.2 μm rated polysulfone membrane. Minimum bubble point was measured by incorporating the drip chamber in an infusion set, priming it with saline and allowing excess liquid to drain by gravity. The MDC with wetted membrane was then pressurized by air to 2 atm. No air was detected at the outlet, indicating a bubble point higher than 2 atm. The MDC was then challenged with a bacteria suspension by aseptically connecting the set to an infusion bag containing sterile saline. An inoculum of pseudomonas diminuta was injected through the injection site so that the final concentration was $10^6$ CFU/ml. The whole bag (100 ml) was then drained through the MDC into an empty, sterile bag. The receiving bag was then tested for sterility. No CFU's were detected.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A drip chamber for intravenous infusion comprising:
   a tubular drip chamber housing having a longitudinal axis;
   a drop former;
   a support member inside said drip chamber housing having a longitudinal axis generally parallel to the longitudinal axis of said drip chamber housing, and at least one support face which has a length and a width;
   a membrane joined to said at least one support face; and
   a filtrate outlet formed at an upper portion of said support member and in fluid communication with said membrane, said filtrate outlet including a bore and being fluidly communicable with an outlet formed at a lower portion of said drip chamber, wherein said membrane is positioned with respect to said outlet of said drip chamber, such that when said drip chamber is primed with infusion solution and in a normal upright orientation, a volume downstream of said membrane is completely filled with infusion solution with no air remaining below said membrane, wherein said downstream volume comprises a volume between said membrane and said at least one support face of said support member, said filtrate outlet, and a conduit disposed inside said support member, said downstream volume fluidly communicating with said bore and with a support member outlet located near an outlet of said drip chamber, and wherein said conduit is narrower than the width of said at least one support face.

2. The drip chamber according to claim 1, wherein said membrane is hydrophilic.

3. The drip chamber according to claim 1, wherein said membrane is bacterially retentive.

4. The drip chamber according to claim 1, wherein said membrane has a surface area of at least about 5 cm$^2$.

5. The drip chamber according to claim 1, wherein said support member outlet is connectable to downstream tubing of an infusion set.

6. The drip chamber according to claim 1, wherein said at least one support face is generally parallel to the longitudinal axis.

7. The drip chamber according to claim 1, wherein said at least one support face is generally perpendicular to the longitudinal axis.

8. The drip chamber according to claim 1, wherein said drip chamber comprises a housing made of a non-PVC material.

9. An intravenous infusion set comprising an infusion bag, a non-vented drip chamber according to claim 1, tubing and clamp on said tubing, wherein said drip chamber and said tubing are automatically and fully primed when said clamp is opened.

10. A drip chamber according to claim 1, constructed such that liquid is in contact with said membrane even when said drip chamber is oriented upside down, thereby enabling continued infusion while upside down.

11. The drip chamber according to claim 1, wherein upon priming of the drip chamber, as liquid enters the volume between said membrane and said at least one support face of said support member, all air in said volume escapes and flows through said filtrate outlet, said conduit and the outlet of said drip chamber in a plug flow regime.

12. The drip chamber according to claim 1, wherein a distal end of the conduit is near the support member outlet and a proximal end of the conduit is near said filtrate outlet.

* * * * *